(12) United States Patent
Feldman

(10) Patent No.: US 7,299,802 B2
(45) Date of Patent: Nov. 27, 2007

(54) CARBON DIOXIDE DELIVERY APPARATUS AND METHOD FOR USING SAME

(76) Inventor: Spencer Feldman, 2599 A Olinda Rd., Makawao, HI (US) 96768

(*) Notice: Subject to any disclaimer, the term of this patent is extended or adjusted under 35 U.S.C. 154(b) by 750 days.

(21) Appl. No.: 10/870,593

(22) Filed: Jun. 17, 2004

(65) Prior Publication Data

US 2004/0255939 A1    Dec. 23, 2004

Related U.S. Application Data

(60) Provisional application No. 60/479,366, filed on Jun. 17, 2003.

(51) Int. Cl.
*A61M 11/00* (2006.01)

(52) U.S. Cl. ............... 128/204.18; 128/200.21; 128/200.23

(58) Field of Classification Search ........... 128/204.18, 128/200.14, 200.21, 200.23, 203.12, 202.22, 128/203.15, 203.21
See application file for complete search history.

(56) References Cited

U.S. PATENT DOCUMENTS

| | | | | |
|---|---|---|---|---|
| 5,201,308 A | * | 4/1993 | Newhouse | 128/203.15 |
| 5,937,852 A | * | 8/1999 | Butler et al. | 128/203.12 |
| 6,548,049 B1 | * | 4/2003 | Cutie et al. | 424/45 |

* cited by examiner

*Primary Examiner*—Steven O. Douglas
(74) *Attorney, Agent, or Firm*—Jackson Walker LLP

(57) ABSTRACT

The present invention relates to a method of increasing the carbon dioxide level in a patient in by administering to the patient an inhalant that comprises a mixture of carbon dioxide and atmospheric air. The method can be used to treat a patient suffering from asthma, allergies, muscle tension, pain, insomnia, and/or mental stress. The present invention also relates to a device that may be used in a method of an inhalant that comprises a mixture of carbon dioxide and atmospheric air to a patient.

12 Claims, 1 Drawing Sheet

CARBON DIOXIDE DELIVERY APPARATUS AND METHOD FOR USING SAME

This application claims priority from 60/479,366, entitled, Method of Treating Asthma, Allergies, Muscle Tension, Pain, and Mental Stress Using Carbon Dioxide.

BACKGROUND OF THE INVENTION

1. Field of the Invention

Applicants' invention relates to a device for administering carbon dioxide and air to a patient, and method for same. More particularly, it relates to a carbon dioxide delivery device acting in concert with an oxygen or ambient air delivery device, to provide a combination of the two to a patient.

2. Background Information

The inhalation of carbon dioxide is known to have a number of beneficial effects. It relaxes smooth muscle tissue which, in the region of the lungs, causes bronchiodilation. Increased levels of carbon dioxide inhibit mast cells from releasing histamine, thus helping decrease inflammation and allergies. It shifts the oxy-hemoglobin curve to the right thereby helping to more efficiently deliver oxygen to the tissues. It increases the threshold required for nerve stimulation thereby decreasing muscle tension and pain, and relieving mental stress. It also can help the lungs' defense against pneumococci infections by acidifying the lung tissue.

As shown by Buteyko, asthma is correlated to low levels of carbon dioxide in the bloodstream and chronic hyperventilation (which causes excessive carbon dioxide loss), and that it can be reversed by teaching patients to breathe slowly, thereby increasing the carbon dioxide level in the bloodstream. It is believed that, in time, the higher level of carbon dioxide in a patient's bloodstream causes the respiratory center of the patient's brain to become less sensitive to blood carbon dioxide, thereby allowing greater levels of carbon dioxide to accumulate in the body before respiration is initiated. The slow breathing method requires time and patient compliance in order to succeed. Unfortunately, many patients lack the discipline required.

Twenty to thirty (20-30) inhalations of carbon dioxide at levels of 30% carbon dioxide and 70% pure oxygen has been proposed by Meduna for treatment of a variety of physiological and psychological disorders. This ratio is designed to result in the patient's loss of consciousness.

Many adults have low carbon dioxide levels (known as hypocapnia). Hypocapnia may be assessed using a capnograph or through blood work. Patients with hypocapnia may experience any or all of its effects, including increased pain, anxiety, insomnia, sleep disorders and asthma, but may not know that their symptoms are related to a common cause. Thus, one objective of the present method of inhaling carbon dioxide as applied to asthma patients is to raise the patient's baseline carbon dioxide, making an asthma attack and/or other hypocapnic disorder less likely.

SUMMARY OF THE INVENTION

The present invention relates to an apparatus and method for increasing the carbon dioxide level in a patient in by administering to the patient an inhalant that comprises a mixture of carbon dioxide and atmospheric air. This method works faster than the Buteyko method and is easier to administer. No breathing exercises are required and the invention provides the long term effect of desensitizing the brain's respiratory center similar to that achieved by slow breathing as well as the short term benefits mentioned above.

The invention also provides many of the benefits achieved by the 30/70 pure oxygen method, without the patient's loss of consciousness. The present invention also relates to a device for administering to a patient an inhalant that comprises a mixture of carbon dioxide and atmospheric air. The device that may be used in the present method of administering carbon dioxide to a patient in need thereof.

A device capable of administering a flow of carbon dioxide to a patient is paired with a means for administering atmospheric air. Many gaseous delivery devices, and in particular carbon dioxide delivery devices, are commercially available and could be used with the present invention. For ease of administration, it is anticipated that small hand-held devices will generally be preferable. Carbon dioxide cartridges, approximately the size of a hand, are also widely available. A carbon dioxide delivery device that is capable of accepting, piercing and sealing carbon dioxide cartridges is well-suited for the present invention in that it is small, easily held and manipulated, and can provide a flow of substantially pure carbon dioxide to a patient. A device capable of providing the required flow is available from REHVHC, Inc. under the brand name "Coflator."

The device may have a filter device incorporated so particulate matter is kept from exiting the mouthpiece. Additionally, the device may have a high-pressure release, or blow-off valve, in case the pressure becomes too high.

The present invention can provide a range of carbon dioxide to be inhaled from about 3% to 100%, with the remainder of the inhalant being atmospheric air. The proportion of carbon dioxide to air can be controlled by venturi ports in the nozzle of a dispenser on the device, or in a mouthpiece bridging the gap between the dispenser and the patient's mouth. The carbon dioxide may be administered to the patient and delivered at a rate of about 1 to about 100 liters per minute, or in another embodiment from 5 to 50 liters per minute. The flow rate, inhalation time, hold time, and inhalation frequency may depend, in part, on the patient's comfort level.

DETAILED DESCRIPTION OF THE PREFERRED EMBODIMENT

Figure 1:
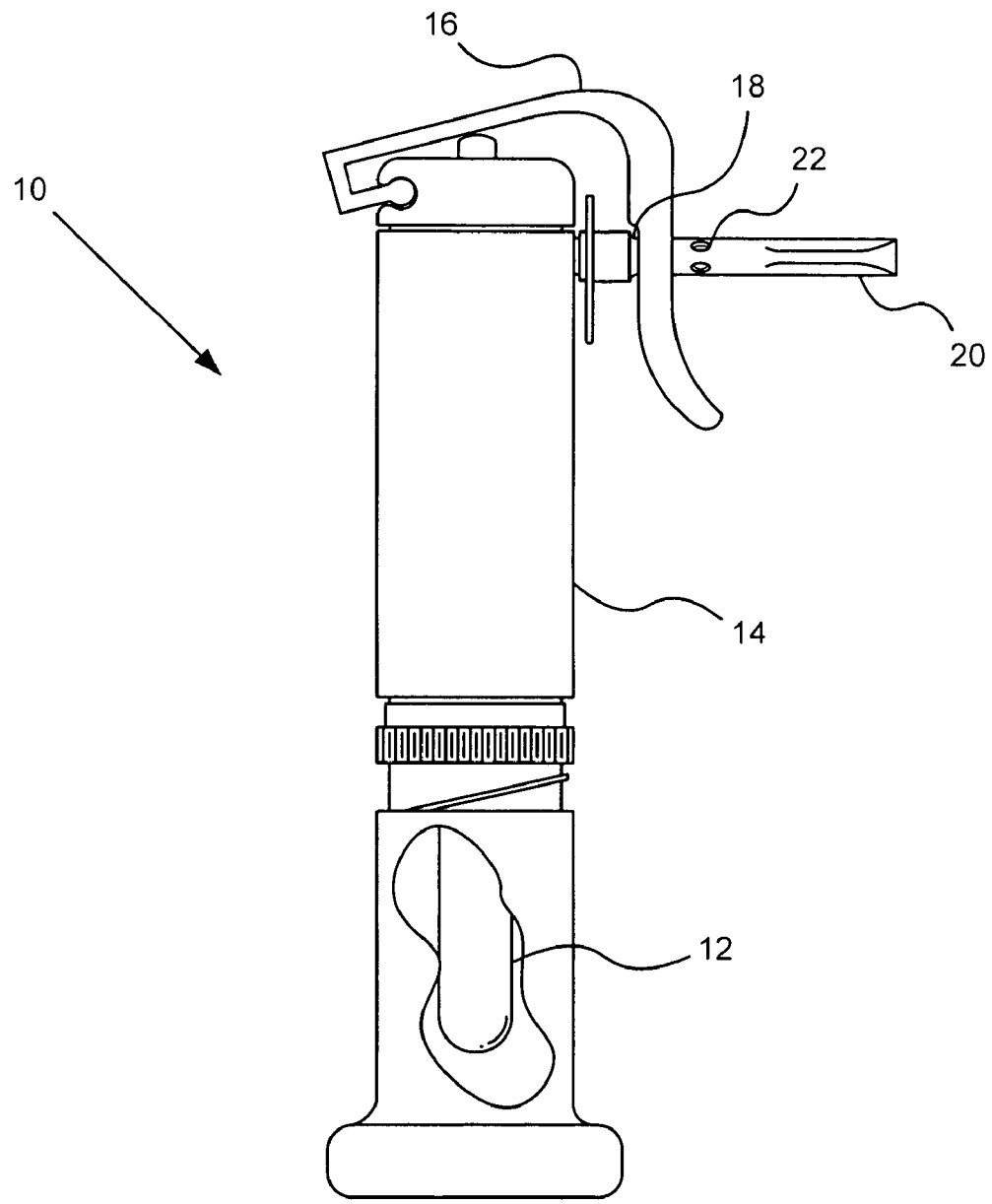
FIG. 1. is a side view of the present invention.

Referring to the figures, FIG. 1. illustrates the present invention. It shows an administration device 10, made up of a gaseous delivery device 14 with a nozzle 18 and a trigger mechanism 16. In order to supply carbon dioxide, the gaseous delivery device 14 must have a carbon dioxide source. While there are many possible sources, most being varying sizes of canisters, popular size canisters hold 12 and 16 grams. Regardless of the size, a cartridge 12 containing carbon dioxide is removably attachable to the gaseous delivery device 14. There are many conceivable embodiments for the gaseous delivery device 14; but, of necessity, the gaseous delivery device 14 should allow communication, or the flow of carbon dioxide, from the cartridge 12 out through the nozzle 18. It is also preferable that the trigger mechanism 16 have an activated position that allows the carbon dioxide to flow from the cartridge 12 out through the nozzle 18, and a deactivated position that stops the flow of carbon dioxide from the cartridge 12. This allows the patient, or the person administering the inhalant to the patient to control the amount of inhalant that the patient receives.

In another embodiment, the trigger mechanism 16 of the administration device 10, once it is moved to the activated position, may release a measured amount of carbon dioxide after which the trigger mechanism 16 automatically returns back to the deactivated position in order to stop the flow of carbon dioxide.

Attached to the nozzle 18 is a mouthpiece 20. The mouthpiece 20 has an opening at the end opposite the nozzle 18 and allows the patient to breathe in the inhalant. The mouthpiece 20 also incorporates one or more venturi ports 22 that allow atmospheric air to enter the mouthpiece and mix with the flowing carbon dioxide, thereby administering an inhalant that is comprised of a mixture of carbon dioxide and atmospheric air.

In an alternative embodiment, a filter (not shown) may be incorporated with either the mouthpiece 20 or the nozzle 18 in order to catch particulate matter and thus prevent it from passing through the nozzle 18 and into the patient.

The cartridge 12 is filled with pressurized carbon dioxide as described above. However, in order to more precisely administer a dosage of inhalant, the cartridge 12 may be filled with substantially pure carbon dioxide. Alternatively, the cartridge 12 may be filled with a pre-mixed inhalant that is comprised of a known percentage of carbon dioxide with the remainder being atmospheric air or oxygen. In this manner, the inhalant percentages of carbon dioxide and atmospheric air may not be known exactly but should be substantially equal to the known percentages.

In alternative embodiments, the administration device 10 may incorporate the use of two cartridges, the first cartridge containing carbon dioxide and a second cartridge containing either oxygen or atmospheric air. The two cartridges are placed in communication with the nozzle 18 allowing the gasses to mix prior to administration to the patient.

The method of using the administration device 10 includes attaching the cartridge 12 to the gaseous delivery device 14. Attaching the mouthpiece 20 to the nozzle 18. Having the patient (not shown) inhale the inhalant from the mouthpiece 20 opposite the nozzle 18. Moving the trigger mechanism 16 from its deactivated position to an activated position, thereby releasing carbon dioxide from the cartridge 12 which flows through the gaseous delivery device 14 out the nozzle 18, through the mouthpiece 20 and into the patient (not shown). As the carbon dioxide passes through the mouthpiece 20, atmospheric air enters the mouthpiece 20 through one or more venturi ports 22 and mixes with the carbon dioxide. The resulting inhalant then enters the patients body.

Anticipated ratios of carbon dioxide to atmospheric air include 3% to 100% carbon dioxide as inhalant and 31% to 100% carbon dioxide in the inhalant. It is anticipated that the inhalant may be administered at a flow rate of 1-to-100 liters per minute. In an alternative embodiment, the inhalant is administered at a flow rate of 5-to-50 liters per minute.

The carbon dioxide and atmospheric air and inhalant described herein is intended to be administered to patients suffering from conditions including asthma, allergies, muscle tension, pain, insomnia, and mental stress.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A device for administering to a patient an inhalant that comprises a mixture of carbon dioxide and atmospheric air, comprising:
    a gaseous delivery device, wherein said gaseous delivery device has a nozzle and a trigger mechanism;
    a cartridge, said cartridge being removably attachable to said gaseous delivery device, and wherein said cartridge contains carbon dioxide;
    said cartridge in communication with said nozzle when said cartridge is attached to said gaseous delivery device;
    said trigger mechanism having an activated position allowing the flow of said carbon dioxide from said cartridge through said nozzle, and said trigger mechanism having an deactivated position stopping the flow of said carbon dioxide from said cartridge through said nozzle; and
    a mouthpiece connected to said nozzle, said mouthpiece having at least one venturi port.

2. The device of claim 1, further comprising a filter capable of preventing particulate matter from passing through the nozzle.

3. The device of claim 1, wherein when said trigger mechanism is moved to said activated position, a measured amount of said carbon dioxide is released, and said trigger mechanism moves automatically back to said deactivated position stopping the flow of said carbon dioxide.

4. The device of claim 1, wherein said carbon dioxide contained in said cartridge is substantially pure carbon dioxide.

5. The device of claim 1, wherein the amount of said carbon dioxide contained in said cartridge is substantially equal to a known percentage, and the remaining percentage is atmospheric air.

6. The device of claim 1, further comprising a second cartridge containing either oxygen or atmospheric air.

7. A method of increasing the carbon dioxide level in a patient, comprising administering to said patient an inhalant comprising a mixture of carbon dioxide and atmospheric air wherein said inhalant is administered using a administration device wherein said administration device comprises:
    a gaseous delivery device, wherein said gaseous delivery device has a nozzle and a trigger mechanism;
    a cartridge, said cartridge being removably attachable to said gaseous delivery device, and wherein said cartridge contains carbon dioxide;
    said cartridge in communication with said nozzle when said cartridge is attached to said gaseous delivery device;
    said trigger mechanism having an activated position allowing the flow of said carbon dioxide from said cartridge through said nozzle, and said trigger mechanism having an deactivated position stopping the flow of said carbon dioxide from said cartridge through said nozzle; and
    a mouthpiece connected to said nozzle, said mouthpiece having at least one venturi port.

8. The method of claim 7, wherein said mixture comprises 3% to 100% carbon dioxide.

9. The method of claim 7, wherein said mixture comprises 31% to 100% carbon dioxide.

10. The method of claim 7, wherein the inhalant is administered at a flow rate of 1 to 100 liters/minute.

11. The method of claim 7, wherein the inhalant is administered at a flow rate of 5 to 50 liters/minute.

12. The method of claim 7, wherein said patient is suffering from a condition selected from asthma, allergies, muscle tension, pain, insomnia, and/or mental stress.

* * * * *